United States Patent [19]

Wong et al.

[11] Patent Number: 5,430,032

[45] Date of Patent: Jul. 4, 1995

[54] BENZOPYRIDO PIPERIDYLIDENE COMPOUNDS, COMPOSITIONS, METHODS OF MANUFACTURE AND METHODS OF USE

[75] Inventors: Jesse K. Wong, Union; John J. Piwinski, Parsippany; Michael J. Green, Skillman, all of N.J.

[73] Assignee: Schering Corporation, Kenilworth, N.J.

[21] Appl. No.: 185,784

[22] Filed: Jan. 21, 1994

Related U.S. Application Data

[63] Continuation of Ser. No. 734,415, Jul. 23, 1991, abandoned.

[51] Int. Cl.$^6$ .................. A61K 31/495; A61K 31/44; C07D 401/00; C07D 491/02
[52] U.S. Cl. .................................... 514/254; 514/291; 544/361; 546/80; 546/89
[58] Field of Search .................. 544/361; 546/80, 89; 514/254, 291

[56] References Cited

U.S. PATENT DOCUMENTS

| | | | |
|---|---|---|---|
| 3,325,501 | 6/1967 | Ettingen et al. | 514/291 |
| 3,326,924 | 6/1967 | Villani | 514/290 |
| 3,717,647 | 2/1973 | Villani | 424/263 |
| 3,803,153 | 4/1974 | Villani | 546/80 |
| 3,803,154 | 4/1974 | Drukker | 514/217 |
| 3,849,410 | 11/1974 | Nakanishi et al. | 514/254 |
| 3,966,944 | 6/1976 | Carter | 424/267 |
| 4,022,902 | 5/1977 | Remy | 546/204 |
| 4,160,031 | 7/1979 | Remy | 546/204 |
| 4,282,233 | 8/1981 | Villani | 546/93 |
| 4,355,036 | 10/1982 | Villani | 546/93 |

(List continued on next page.)

FOREIGN PATENT DOCUMENTS

| | | |
|---|---|---|
| 638971 | 4/1964 | Belgium . |
| 644121 | 8/1964 | Belgium . |

(List continued on next page.)

OTHER PUBLICATIONS

Villani et al., Journal of Medicinal Chemistry, vol. 15, No. 7, pp. 750–754 (1972).
Arzn. Forsh., 36, 1311–1314 (1986).

*Primary Examiner*—Cecilia Tsang
*Attorney, Agent, or Firm*—Henry C. Jeanette

[57] ABSTRACT

Disclosed is a compound of Formula I:

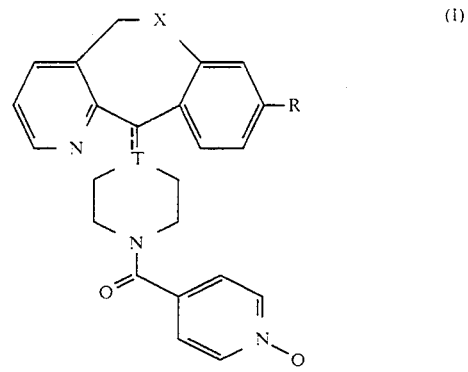

or a pharmaceutically acceptable salt or solvate thereof, wherein: R is selected from the group consisting of: H, Cl, Br, F, and I; T represents C or N with the dotted line attached to T representing a double bond when T is C and being absent when T is N; and X represents O or S with the proviso that T is N when X is O.

Also disclosed is a pharmaceutical composition comprising a compound of Formula I and a pharmaceutically acceptable carrier.

Further disclosed is a method of treating asthma, allergy and/or inflammation comprising administering to a mammal in need of such treatment an anti-asthmatic, anti-allergic and/or an anti-inflammatory, respectively, effective amount of a compound of Formula I.

11 Claims, No Drawings

U.S. PATENT DOCUMENTS

| | | | |
|---|---|---|---|
| 4,609,664 | 9/1986 | Hasspacher | 514/324 |
| 4,826,853 | 5/1989 | Piwinski et al. | 514/290 |
| 4,889,858 | 12/1989 | Uno et al. | 546/203 |
| 4,912,222 | 3/1990 | Griffith et al. | 546/203 |
| 5,089,496 | 2/1992 | Piwinski et al. | 514/253 |
| 5,104,876 | 4/1992 | Piwinski et al. | 514/254 |
| 5,151,423 | 9/1992 | Piwinski et al. | 514/254 |

FOREIGN PATENT DOCUMENTS

| | | |
|---|---|---|
| 780443 | 3/1968 | Canada . |
| 0042544 | 12/1981 | European Pat. Off. . |
| 0047226 | 3/1982 | European Pat. Off. . |
| 0371805 | 6/1990 | European Pat. Off. . |
| 17764 | 4/1964 | Ireland . |
| WO88/03138 | 5/1988 | WIPO . |
| WO89/10363 | 11/1989 | WIPO . |
| WO89/10369 | 11/1989 | WIPO . |
| WO90/13548 | 11/1990 | WIPO . |
| 13548 | 11/1990 | WIPO . |
| WO92/00293 | 1/1992 | World Intl. Prop. Off. . |
| 00293 | 1/1992 | WIPO . |

BENZOPYRIDO PIPERIDYLIDENE COMPOUNDS, COMPOSITIONS, METHODS OF MANUFACTURE AND METHODS OF USE

REFERENCE TO RELATED APPLICATION

The present application is the United States national application corresponding to International Application No. PCT/US 92/05850, filed 17 Jul. 1992, and designating the United States, which PCT application is in turn a continuation of U.S. application Ser. No. 07/734,415, filed 23 Jul. 1991, now abandoned, the benefit of which applications are claimed pursuant to the provisions of 35 U.S.C. 120, 363 and 365 (C).

This application is related to International Publication Number WO 89/10369 which published on Nov. 2, 1989 on International Application Number PCT/US89/01688 which was filed on Apr. 26, 1989 and which has priority to U.S. application Ser. No. 187, 604, abandoned which was filed Apr. 28, 1988, the disclosure of which is incorporated herein by reference thereto. This application is also related to U.S. application Ser. No. 07/704,534, abandoned which was filed on May 23, 1991, the disclosure of which is incorporated herein by reference thereto.

BACKGROUND OF THE INVENTION

U.S. Pat. Nos. 3,326,924, 3,717,647 and 4,282,233, European published Application No. 0042544 and Villani et al., Journal of Medicinal Chemistry, Vol. 15, No. 7, pp 750-754 (1972) and Arzn. Forsh 36 1311-1314 (1986) describe certain 11-(4-piperidylidene)-5H-benzo[5,6]cyclohepta[1,2-b]pyridines as antihistamines. U.S. Pat. No. 4,355,036 describes certain N-substituted piperidylidene compounds.

International Publication Number WO 89/10369 discloses compounds of the formula:

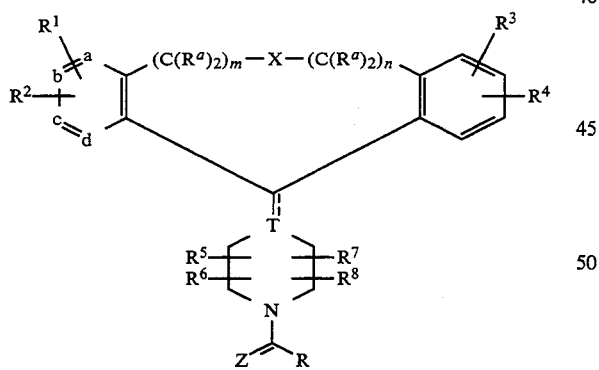

wherein:
one of a, b, c and d represents nitrogen or —NR$^{11}$—, wherein R$^{11}$ is O$^-$, —CH$_3$ or —(CH$_2$)$_p$CO$_2$H wherein p is 1 to 3, and the remaining a, b, c and d groups are CH which may be substituted with R$^1$ or R$^2$;

R$^1$ or R$^2$ may be the same or different and each independently represents halo, —CF$_3$, —OR$^{10}$, —C(O)R$^{10}$, —S(O)$_e$R$^{12}$ wherein e is 0, 1, or 2, —N(R$^{10}$)$_2$, —NO$_2$, —SH, —CN, —OC(O)R$^{10}$, —CO$_2$R$^{10}$, —OCO$_2$R$^{12}$, —NR$^{10}$C(O)R$^{10}$, alkyl, alkenyl or alkynyl, which alkyl or alkenyl groups may be substituted with halo, —OR$^{10}$ or —CO$_2$R$^{10}$, or R$^1$ and R$^2$ may together form a benzene ring fused to the pyridine ring;

R$^{10}$ represents H, alkyl or aryl;

R$^{12}$ represents alkyl or aryl;

R$^3$ and R$^4$ may be the same or different and each independently represents H or any of the substituents of R$^1$ and R$^2$, or R$^3$ and R$^4$ may be taken together to represent a saturated or unsaturated C$_5$ to C$_7$ ring fused to the benzene ring;

R$^5$, R$^6$, R$^7$, and R$^8$ each independently represents H, —CF$_3$, —CO$_2$R$^{10}$, —C(O)R$^{10}$, alkyl or aryl, which alkyl or aryl may be substituted with —OR$^{10}$, —SR$^{10}$, —N(R$^{10}$)$_2$, —NO$_2$, —C(O)R$^{10}$, —OC(O)R$^{12}$, —CO$_2$R$^{10}$ and —OPO$_3$(R$^{10}$)$_2$, or one of R$^5$, R$^6$, R$^7$, and R$^8$ may be taken in combination with R as defined below to represent —(CH$_2$)$_r$— wherein r is 1 to 4, said combination being optionally substituted with lower alkyl, lower alkoxy, —CF$_3$ or aryl, or R$^5$ may be combined with R$^6$ to represent =O or =S, and/or R$^7$ may be combined with R$^8$ to represent =O or =S;

T represents carbon or nitrogen, with the dotted line attached to T representing an optional double bond when T is carbon;

m and n are integers 0, 1, 2, or 3, such that the sum of m plus n equals 0 to 3;

when m plus n equals 1, X represents —O—, —S(O)$_e$— wherein e is 0, 1 or 2, —NR$^{10}$—, —C(O)NR$_{10}$—, —NR$^{10}$C(O)—, —C(S)NR$^{10}$—, —NR$^{10}$C(S)—, —C(O)$_2$— or —O$_2$C—, wherein R$^{10}$ is as defined above;

when m plus n equals 2, X represents —O—, —S(O)$_e$ wherein e is 0, 1 or 2, or —NR$^{10}$—;

when m plus n represents 0, X can be any substituent for m plus n equalling 1 and X can also be a direct bond, cyclopropylene or propenylene;

when m plus n equals 3 then X equals a direct bond;

each R$^a$ may be the same or different, and each independently represents H, lower alkyl or phenyl;

Z represents =O, =S or =NR$^{13}$ with R$^{13}$ equal to R$^{10}$ or —CN, wherein R$^{10}$ is as defined above, such that (a) when Z is O, R may be taken in combination with R$^5$, R$^6$, R$^7$ or R$^8$ as defined above, or R represents H, alkyl, aryl, —SR$^{12}$, —N(R$^{10}$)$_2$, cycloalkyl, alkenyl, alkynyl or —D wherein —D represents heterocycloalkyl,

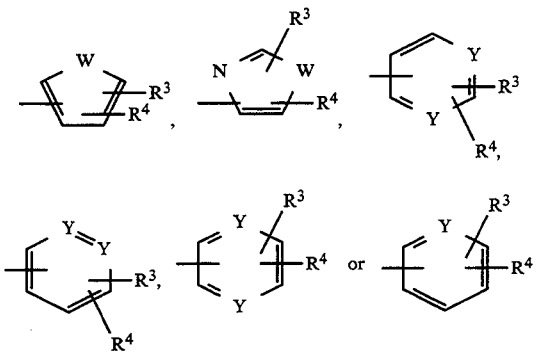

wherein R$^3$ and R$^4$ are as previously defined, and W is O, S or NR$^{10}$, and wherein Y is N or NR$^{11}$, said cycloalkyl, alkyl, alkenyl and alkynyl being optionally substituted with from 1-3 groups selected from halo, —CON(R$^{10}$)$_2$, aryl, —CO$_2$R$^{10}$, —$OR^{14}$, —$SR^{14}$, —$N(R^{10})_2$, —$N(R^{10})CO_2R^{10}$, —$COR^{14}$, —$NO_2$ or —D, wherein —D and $R^{10}$ are as defined above and $R^{14}$ represents $R^{10}$, —$(CH_2)_rOR^{10}$ or —$(CH_2)_qCO_2R^{10}$ wherein r is 1 to 4, q is 0 to 4; said alkenyl and alkynyl R groups not containing —OH, —SH, or —$N(R^{10})_2$ on a carbon in a double or triple bond respectively; and (b) when Z represents =S, R represents in addition to those R groups above, aryloxy or alkoxy; and (c) where Z represents =$NR^{13}$, R represents H, alkyl, aryl, $N(R^{10})_2$, cycloalkyl, alkenyl or alkynyl.

WO 89/10369 generically discloses compounds which can have the structure:

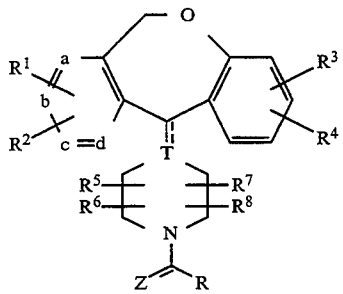

wherein Z can be O and R can be:

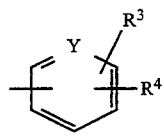

wherein Y can be $NR^{11}$ and $R^{11}$ can be —$O^-$; however, no specific compounds are disclosed with this structure.

U.S. Pat. No. 4,826,853 issued to Piwinski et al. on May 2, 1989 is the priority document for WO 88/03138 which published on May 5, 1988. WO 88/03138 discloses compounds of the formula

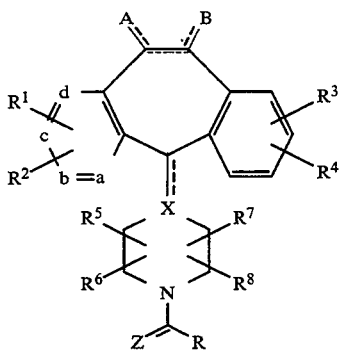

or a pharmaceutically acceptable salt or solvate thereof, wherein:

one of a, b, c and d represents N or $NR^9$ where $R^9$ is O —$CH_3$ or —$(CH_2)_nCO_2H$ where n is 1 to 3, and the remaining a, b, c and d groups are CH, which remaining a, b, c and d groups optionally may be substituted with $R^1$ or $R^2$;

$R^1$ and $R^2$ may be the same or different and each independently represents halo, —$CF_3$, —$OR^{10}$, —$COR^{10}$, —$SR^{10}$, —$N(R^{10})_2$, —$NO_2$, —$OC(O)R^{10}$, —$CO_2R^{10}$, —$OCO_2R^{11}$, alkynyl, alkenyl or alkyl, which alkyl or alkenyl group may be substituted with halo, —$OR^{10}$ or —$CO_2R^{10}$;

$R^3$ and $R^4$ may be the same or different and each independently represents H, any of the substituents of $R^1$ and $R^2$, or $R^3$ and $R^4$ together may represent a saturated or unsaturated fused $C_5$-$C_7$ ring;

$R^5$, $R^6$, $R^7$ and $R^8$ each independently represent H, —$CF_3$, alkyl or aryl, which alkyl or aryl may be substituted with —$OR^{10}$, —$SR^{10}$, —$N(R^{10})_2$, —$NO_2$, —$COR^{10}$, —$OCOR^{10}$, —$OCO_2R^{11}$, —$CO_2R^{10}$, —$OPO_3R^{10}$ or one of $R^5$, $R^6$, $R^7$ and $R^8$ may be taken in combination with R as defined below to represent —$(CH_2)_r$— where r is 1 to 4 which may be substituted with lower alkyl, lower alkoxy, —$CF_3$ or aryl;

$R^{10}$ represents H, alkyl or aryl;

$R^{11}$ represents alkyl or aryl;

X represents N or C, which C may contain an optional double bond to carbon atom 11;

the dotted line between carbon atoms 5 and 6 represents an optional double bond, such that when a double bond is present, A and B independently represent H, —$R^{10}$, —$OR^{11}$ or —$OC(O)R^{10}$, and when no double bond is present between carbon atoms 5 and 6, A and B each independently represent $H_2$, —$(OR^{10})_2$, alkyl and H, (alkyl)$_2$, —H and —$OC(O)R^{10}$, H and —$OR^{10}$, =O, aryl and H, =$NOR^{10}$ or —O—$(CH_2)_p$—O—where p is 2, 3 or 4 and $R^{10}$ is as previously defined;

Z represents O, S or $H_2$ such that (a) when Z is O, R may be taken in combination with $R^5$, $R^6$, $R^7$ or $R^8$ as defined above, or R represents H, aryl, alkyl, —$SR^{11}$, —$N(R^{10})_2$, cycloalkyl, alkenyl, alkynyl or —D wherein —D represents heterocycloalkyl,

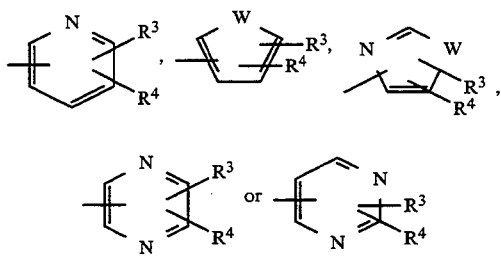

wherein $R^3$ and $R^4$ are as previously defined and W is O, S or $NR^{10}$ wherein $R^{10}$ is as defined above, said cycloalkyl, alkyl, alkenyl and alkynyl being optionally substituted with from 1-3 groups selected from halo, —$CON(R^{10})_2$ aryl, —$CO_2R^{10}$, —$OR^{12}$, —$SR^{12}$, —$N(R^{10})_2$, —$N(R^{10})CO_2R^{10}$, —$COR^{12}$, —$NO_2$ or —D, wherein —D and $R^{10}$ are as defined above and $R^{12}$ represents $R^{10}$, —$(CH_2)_mOR^{10}$ or —$(CH_2)_qCO_2R^{10}$ wherein $R^{10}$ is as previously defined, m is 1 to 4 and q is 0 to 4, said alkenyl and alkynyl R groups not containing —OH, —SH or —$N(R^{10})_2$ on a carbon containing a double or triple bond respectively;

(b) when Z represents S, R represents in addition to those R groups above, aryloxy or alkoxy; and (c) when Z represents $H_2$, R represents —$COOR^{10}$, —E—$COOR^{10}$ or —E—$OR^{12}$ where E is alkanediyl which may be substituted with —$OR^{10}$, —$SR^{10}$, —$N(R^{10})_2$ or —D where D, $R^{10}$ and $R^{12}$ are as previously defined. These compounds are disclosed as being useful in the treatment of allergy and inflammation.

During the course of our research on the compounds disclosed in WO 88/03138, we generally found that the compounds having a carbonyl group (Z=O) attached to the piperidyl, piperidylidenyl or piperazinyl nitrogen atom were much stronger antagonists of platelet activating factor (PAF) than the compounds having a $CH_2$ group (Z=$H_2$) attached thereto.

WO 90/13548 published on Nov. 15, 1990 on PCT/US90/02251 which was filed on Apr. 30, 1990 and claims priority to U.S. application Ser. No. 345,604 filed May 1, 1989 discloses compounds similar in structure to the compounds disclosed in WO 88/03138 with the difference being that the R group represents an N-oxide heterocyclic group of the formula (i), (ii), (iii), or (iv):

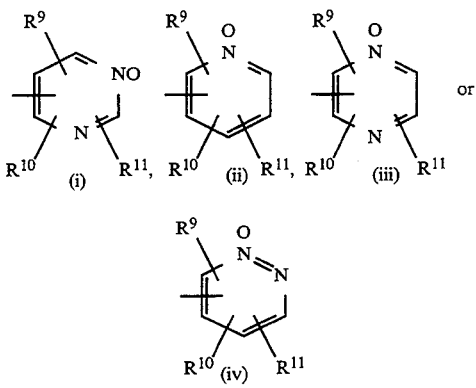

wherein $R^9$, $R^{10}$, and $R^{11}$ can be, amongst other groups, H.

Copending U.S. application Ser. No. 625,261 filed on Dec. 10, 1990 is related to WO 90/13548.

The following references have disclosed oxygen or sulfur in the bridgehead of the three ring portion of the molecule:

(1) Canadian Application 780,443, published in the name of Sandoz Patents Ltd.;
(2) Eire 17764, published Apr. 5, 1964 in the name of Sandoz Patents Ltd.;
(3) European Patent Application 81816337.6, Sandoz A. G., published March 10, 1982;
(4) Belgian Application 638,971, Sandoz S. A., published Apr. 21, 1964;
(5) Belgian Application 644, 1 21, Sandoz S. A., published Aug. 20, 1964;
(6) U.S. Pat. No. 4,609,664, issued to Hasspacher on Sep. 2, 1986;
(7) U.S. Pat. No. 3,966,944, issued to Carter on Jun. 29, 1976;
(8) U.S. Pat. No. 3,803,153, issued to Villani on Apr. 9, 1974;
(9) U.S. Pat. No. 3,803,154, issued to Drukker on Apr. 9, 1974; and
(10) U.S. Pat. No. 3,325,501, issued to Ettinsen et al. on Jun. 13, 1967.

None of references (1) to (10) above disclose substitution on the piperidylidene nitrogen similar to that described below for the compounds of this invention.

European Patent Application, Publication No. 0 371 805, published Jun. 6, 1990, priority based on Japanese 303461/88 (30 Nov. 1988) and JP64059/89 (16 Mar. 1989) discloses compounds useful as hypotensives having the formula:

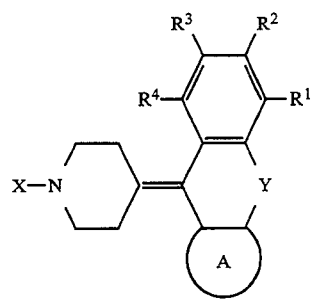

wherein:
any of $R^1$, $R^2$, $R^3$ and $R^4$ may be the same or different from each other and each independently represents a hydrogen atom or other substituent;

X represents an aralkyl- or aryl-containing group having from 6 to 30 carbon atoms or an alkyl group having from 4 to 30 carbon atoms or a cycloalkyl-containing group, which may optionally have substituent(s) and which may be substituted by hetero atom(s) or hetero atom-containing organic group(s) said alkyl group optionally containing unsaturated bond(s);

Y represents a heteroatom or an optionally substituted alkylene chain, the alkylene chain optionally containing hetero atom(s) or unsaturated bond(s); and A represents an optionally substituted condensed aromatic or heterocyclic ring.

European Patent Publication No. 0 371 805 also discloses that if present, the aromatic ring of X or A is benzene, pyridine, pyridazine, or pyrazine, amongst others (see page 3 at about lines 35–40).

Amongst the specific compounds disclosed in European Patent Publication No. 0 371 805, there is included:

(1) 4-(5H-Dibenzo[a,d]cyclohepten-5-ylidene)-1-(2-Picolyl)piperidine;
(2) 4-(5H-Dibenzo[a,d]cyclohepten-5-ylidene)-1-(3-Picolyl)piperidine; and
(3) 4-(5H-Dibenzo[a,d]cyclohepten-5-ylidene)-1-(4-Picolyl)piperidine (see page 34 at about lines 36–38). It is believed the structures of these compounds are:

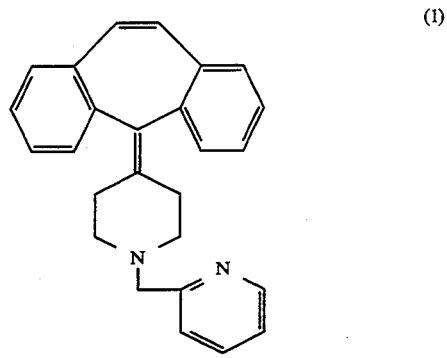

(1)

-continued (2)
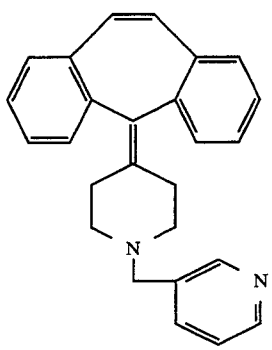

(3)
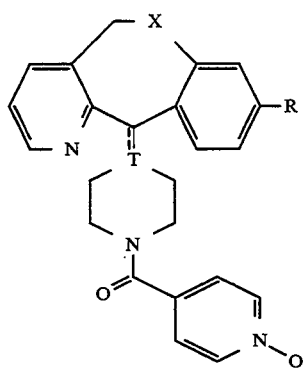

SUMMARY OF THE INVENTION

Surprisingly and unexpectedly it has been discovered that a specific group Of compounds, generically disclosed but not specifically disclosed in WO 89/10369, are very potent selective PAF antagonists. This specific group of compounds, represented by Formula I below, are in general more potent in their anti-PAF activity and also are weaker antihistamines then known compounds having a similar structure (see, for example, U.S. Pat. No. 4,826,853, WO 88/03138, WO 90/13548, and WO 89/10369).

This invention provides compounds represented by Formula I:

(I)

or a pharmaceutically acceptable salt or solvate thereof, wherein:
R represents H or a halogen atom selected from the group consisting of: Cl, Br, F, and I;
T represents C or N with the dotted line attached to T representing a double bond when T is C and being absent when T is N; and X represents O or S with the proviso that T is N when X is O.

One preferred embodiment of this invention provides compounds of Formula IA:

(IA)

wherein R is as defined for Formula I, and most preferably R is Cl.

Another preferred embodiment of this invention provides compounds of Formula IB:

(IB)

wherein X and R are as defined for Formula I, and most preferably R is Cl.

Representative compounds of this invention include:

(IA1)
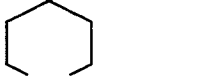

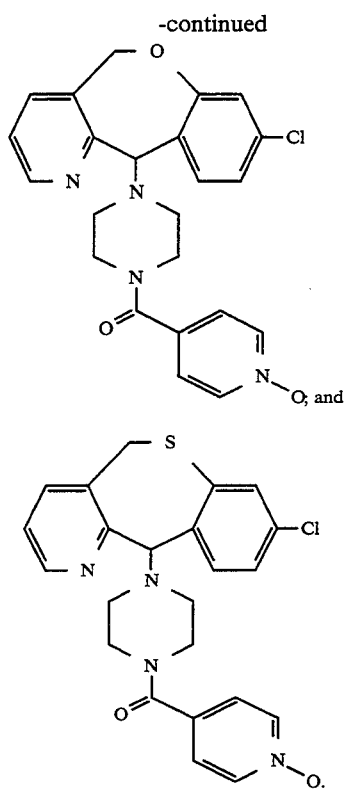

Those skilled in the art will appreciate that the N-oxide heterocyclic ring may be equally represented as:

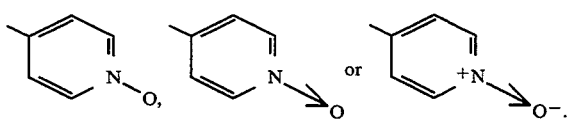

This invention also provides a pharmaceutical composition comprising a compound represented by Formula I and a pharmaceutically acceptable carrier.

This invention further provides a method of treating asthma, allergy and/or inflammation in a mammal, preferably a human, in need of such treatment, said method comprising administering an anti-asthmatic, anti-allergic and/or anti-inflammatory effective amount, respectively, of a compound of Formula I. Preferably the compound is administered as a pharmaceutical composition of this invention.

DETAILED DESCRIPTION OF THE INVENTION

Certain compounds of this invention may exist in different isomeric (e.g., enantiomers and diastereoisomers) as well as conformational forms. This invention contemplates all such isomers both in pure form and in admixture, including racemic mixtures.

The compounds of the invention of Formula I can exist in unsolvated as well as solvated forms, including hydrated forms, e.g., hemihydrate. In general, the solvated forms, with pharmaceutically acceptable solvents such as water, ethanol and the like, are equivalent to the unsolvated forms for purposes of this invention.

Compounds of this invention are basic in nature, i.e., all compounds possess a pyridine ring and in some cases a piperazine ring. Hence, they may form pharmaceutically acceptable salts, e.g., acid addition salts. For example, the pyrido-nitrogen atom may form salts with strong acid. Examples of suitable acids for salt formation are hydrochloric, sulfuric, phosphoric, fumaric, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base forms for purposes of this invention.

All such base salts (e.g. pyridinyl or piperazine nitrogen salts) are intended to be pharmaceutically acceptable salts within the scope of the invention and all acid and base salts are considered equivalent to the free forms of the corresponding compounds for purposes of the invention.

The following processes may be employed to produce compounds of Formula I.

Processes A To E For The Preparation Of Compounds Of Formula I

In general the processes used to prepare the various compounds of the invention (Formula I) are disclosed in WO 89/10369, the disclosure of which is incorporated herein by reference thereto.

Process A

In the preferred method, a compound of Formula II can be coupled with isonicotinic acid N-oxide in the presence of a coupling agent, such as 1-(3-dimethylaminopropyl)-3-ethyl carbodiimide hydrochloride (DEC), N,N'-dicyclohexylcarbodiimide (DCC) or N,N'-carbonyl diimidazole (CDI), to produce compounds of Formula I:

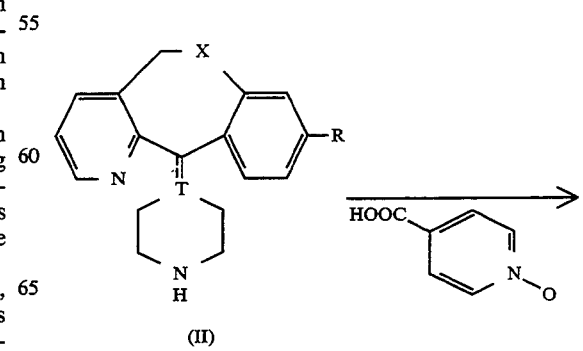

-continued

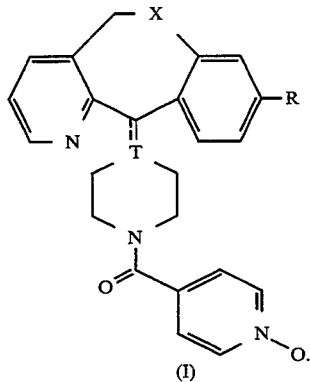

The reaction is usually conducted in an inert solvent, such as tetrahydrofuran or methylene chloride, at a temperature between 0° C. and reflux, usually at room temperature. When the coupling agent is DCC or DEC, the reaction is preferably run in the presence of 1-hydroxybenzotriazole (HOBT).

Process B

A compound of Formula II may also be reacted with a compound of Formula III in the presence of a base to produce compounds of Formula I:

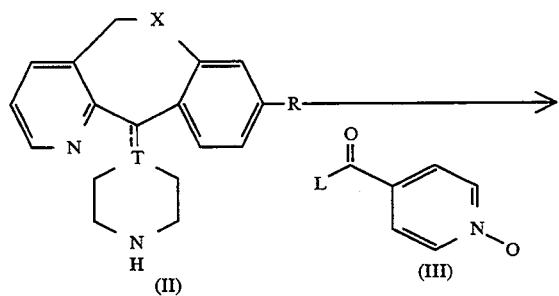

Representative examples of bases are pyridine and triethylamine. L designates a suitable leaving group. For example, a compound of Formula III may be an acyl halide (e.g., L is Cl), in which case compound III can be generated from the corresponding carboxylic acid using oxalyl chloride or similar agent.

Process C

Compounds of Formula I may also be prepared by reacting a compound of Formula IV with a compound of Formula III:

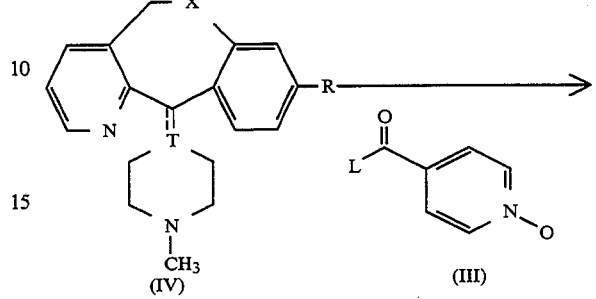

Preferably this reaction may be run in the presence of a suitable nucleophile (e.g., LiI, and the like) in an inert solvent (e.g., toluene, dioxane or xylenes). A suitable base, such as triethylamine or potassium carbonate may be added, and heating may usually be required. Typically, a temperature ranging from about 50° to about 150° C. (preferably about 100° to about 120° C.) may be utilized depending on the boiling point of the solvent.

Process D

Certain compounds of Formula IB (i.e., T is nitrogen) may also be prepared by alkylation of a compound of Formula VI with a compound of Formula V. In Process D, L is a suitable leaving group such as a halide (e.g., L=Cl, Br, I) or other leaving group (e.g., tosyloxy or mesyloxy):

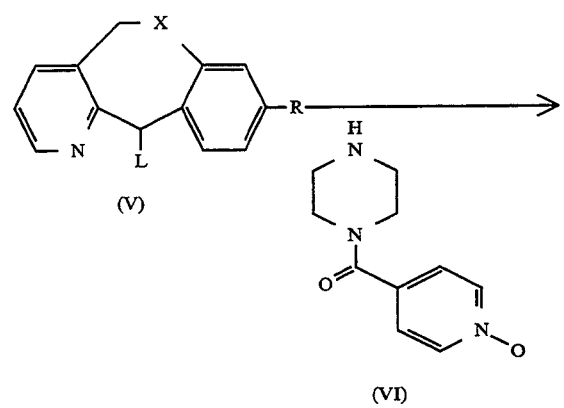

-continued

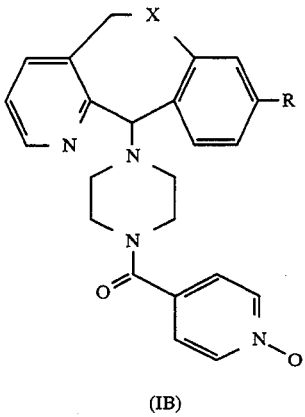

(IB)

The reaction may be conducted in an inert solvent such as tetrahydrofuran or toluene, typically at a temperature range of ambient to reflux depending on the solvent of choice. A suitable base may be added such as triethylamine or potassium carbonate, although the reaction may proceed without the addition of base.

Process E

An alternative route for generating a compound of Formula IB (i.e., T is nitrogen) may be by reductive amination of compound VII with a compound of the formula VI:

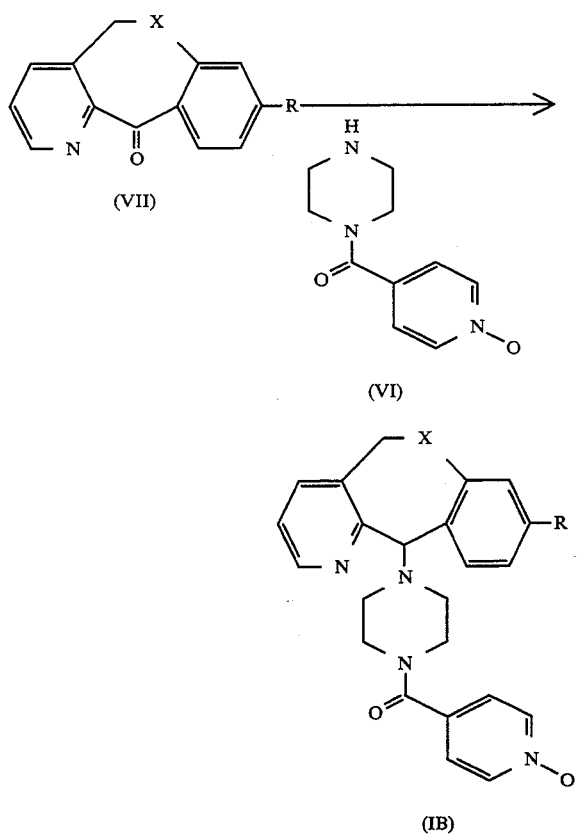

The reaction may be carded out in a polar solvent such as an alcohol (e.g., methanol or ethanol) and optionally in the presence of a water scavenger such as 3 Å molecular sieves. The presence of a reducing agent such as NaCNBH$_3$ or H$_2$/Pd-C is necessary for reduction of the intermediate Schiff base. Temperatures for the reaction are typically held between 0°–100° C. depending on the solvent employed.

Preparation Of Intermediate Compounds

Preparation of Intermediate Compounds Wherein T is Carbon and X is Sulfur

Compounds of the general Formula IIA (i.e., T=C, X=S) can be prepared by cleaving a carbamate group (COOR' wherein R' is an alkyl group, such as ethyl, or an aryl group, such as phenyl) from the corresponding carbamates of Formula VIII. This can be accomplished by a variety of methods including acid hydrolysis (e.g., HCl) or base hydrolysis (e.g., KOH) as long as R' is a group which does not prevent the cleavage reaction. Alternatively, depending on the nature of R', as determined by one who is skilled in the art, a compound of Formula VIII may be treated with an organometallic reagent (e.g., CH$_3$Li wherein R' is an alkyl group such as ethyl) or a reductive reagent (e.g., Zn in acid where R' is 2,2,2-trichloroethyl) in order to produce a compound of Formula IIA.

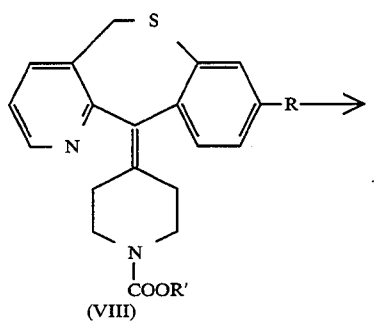

(VIII)

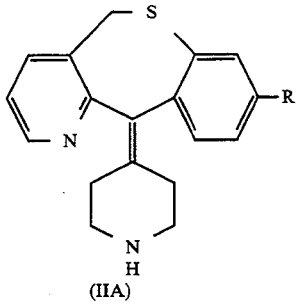

(IIA)

Compounds of Formula VIII can be prepared from the corresponding N-methyl compounds of Formula IVA by treating compounds of Formula IVA with a suitable chlorocarbamate containing R' (e.g., ClCOOR'). The reaction can usually be carded out at an elevated temperature (e.g., about 70° to about 100° C.) by heating a compound of Formula IVA in an inert solvent, such as toluene, in the presence of the chlorocarbamate and optionally with a base such as triethylamine. This procedure is described for similar compounds in U.S. Pat. Nos. 4,282,233 and 4,335,036, the disclosures of each being incorporated herein by reference thereto.

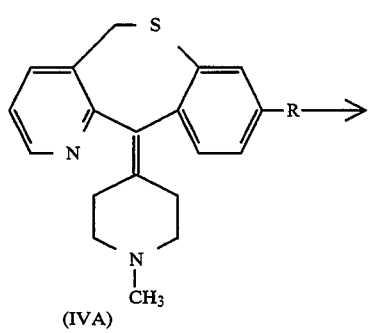

(IVA)

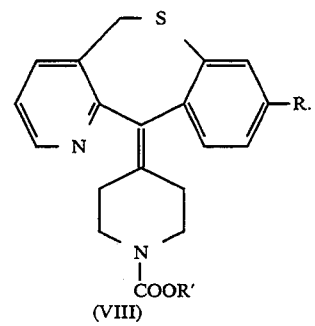

(VIII)

Those skilled in the art will appreciate that there are other methods for convening a compound of Formula IVA to a compound of Formula IIA. For example, treatment of a compound of Formula IVA with phosgene to produce a compound of the Formula IX followed by hydrolysis with aqueous acid may produce compounds of Formula IIA. Alternatively, treatment of a compound of Formula IVA with cyanogen bromide (i.e., BrCN) via Von Braun reaction conditions would provide a nitrile of Formula X as illustrated below. Subsequent hydrolysis of the nitrile of Formula X under either aqueous basic or aqueous acidic conditions would produce a compound of Formula IIA.

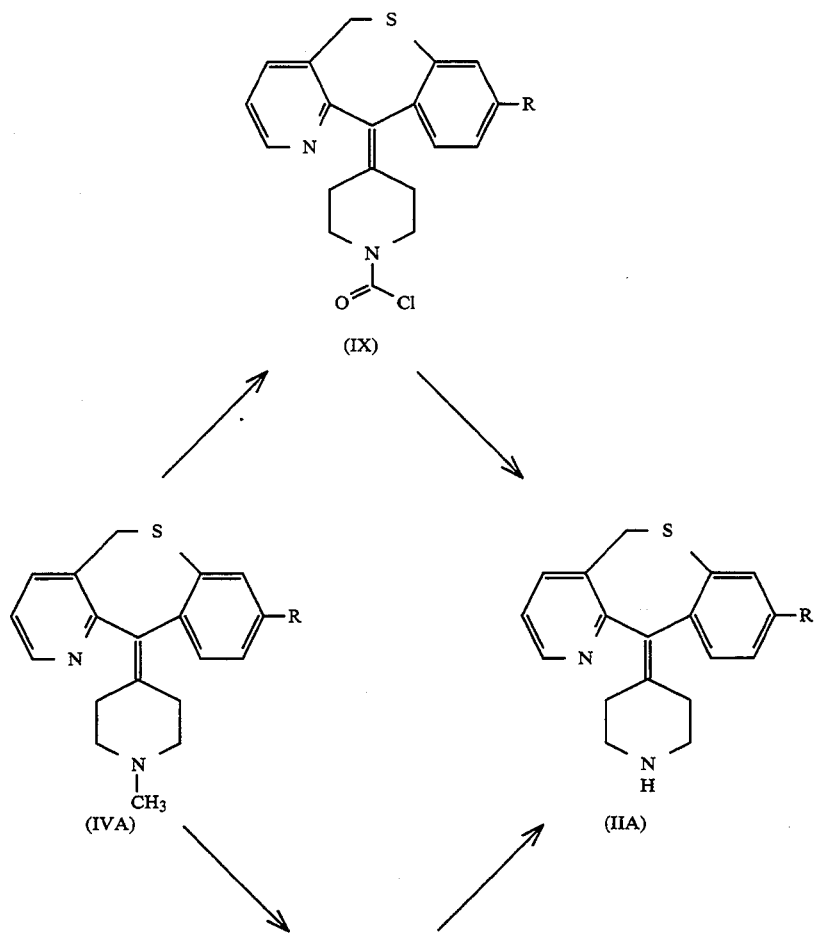

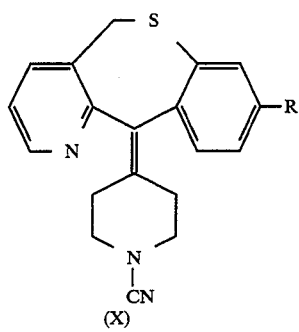

(X)

Compounds of Formula IVA can be prepared from a corresponding alcohol of Formula XI by using either acidic or basic conditions in accordance with methods well known in the art. For example, treatment of a compound of Formula XI with trifluoromethanesulfonic acid and heating (about 40° to about 60° C.) results in dehydration of the alcohol to produce the olefin of Formula IVA. Other acids such as polyphosphoric acid or sulfuric acid may also be employed.

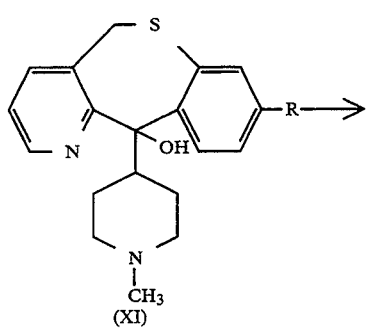

(XI)

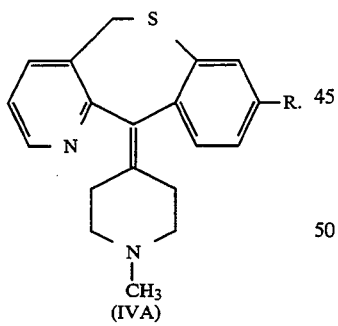

(IVA)

The alcohol of Formula XI can be prepared via the treatment of a ketone of Formula VIIA with the Grignard reagent derived from N-methyl-4-chloropiperidine in an inert solvent such as tetrahydrofuran. Other organometallic reagents known in the art may also be used; for example, N-methyl-4-lithiopiperidine. The reaction may be conducted at or below room temperature (e.g., about −15° to about 25° C.); however, the reaction mixture may be refluxed if necessary. Quenching the reaction with a mild acid (such as aqueous ammonium chloride) or water produces an alcohol of Formula XI. The Grignard reagent may be prepared from the corresponding halo derivative using methods well known in the art.

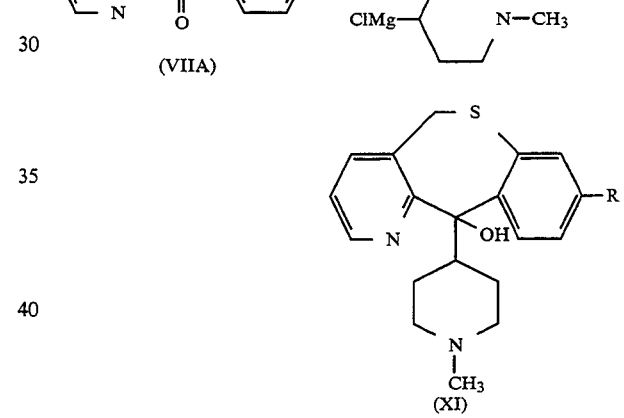

(VIIA)

(XI)

Preparation Of Intermediate Compounds Wherein T is Nitrogen and X is Sulfur or Oxygen Compounds of Formula XIII can be prepared by alkylation of a compound of Formula XII with a compound of Formula V wherein L is a suitable leaving group such as a halide (e.g., L=Cl, Br, I) or other leaving group (e.g., tosyloxy or mesyloxy) and R″ is either hydrogen or a carbamate (—CO₂R′ where R′ is as defined above):

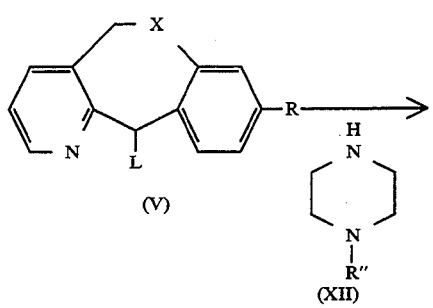

(V)

(XII)

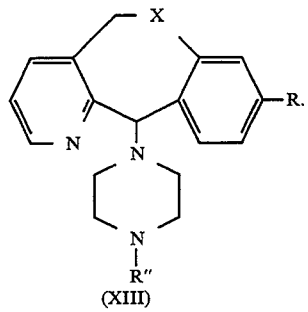

(XIII)

The reaction can be conducted in an inert solvent such as tetrahydrofuran or toluene, typically at a temperature range of ambient to reflux depending on the solvent of choice. The piperazine derivative XII is often employed in excess although this is not necessary. A suitable base may be added such as triethylamine or potassium carbonate, although the reaction may proceed without it. Note that in this reaction when R" is hydrogen then compound XIII is a compound of Formula IIB (i.e., T=N). However, if R" is a carbamate, then the carbamate must be subsequently removed in order to provide a compound of Formula IIB. This is accomplished in the same manner as described above for the conversion of compound VIII to compound IIA.

Alternatively, a compound of the Formula XIII may be prepared from a compound XII by reductive amination of compound VII:

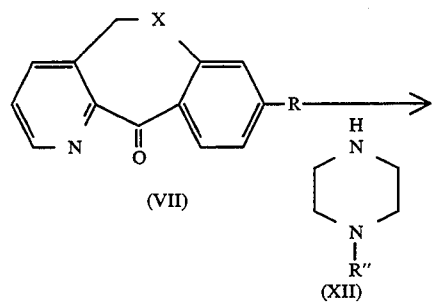

The reaction is typically carded out in a polar solvent such as an alcohol (e.g., methanol or ethanol), optionally in the presence of a water scavenger such as 3 Å molecular sieves. The presence of a reducing agent such as NaCNBH$_3$ or H$_2$/Pd-C is necessary for reduction of the intermediate Schiff base. Temperatures for the reaction are typically held between 0°–100° C. depending on the solvent employed. As is noted above, when R" is hydrogen then compound XIII is a compound of Formula IIB (i.e., T=N). However, if R" is a carbamate, then the carbamate must be subsequently removed in order to provide a compound of Formula IIB. This is accomplished in the same manner as described above for the conversion of compound VIII to compound IIA.

Compound V may be prepared from the corresponding alcohol XIV. A variety of methods may be used to convert an alcohol to the corresponding halide depending on the halide desired and the nature of the alcohol. For example, if the chloro derivative (L=Cl) is desired, one can simply treat the alcohol XIV with thionyl chloride in an inert solvent such as toluene to produce the corresponding chloro derivative of V. Alternatively, one may generate the corresponding tosyloxy or mesyloxy derivatives of V (L=—OSO$_2$C$_6$H$_4$CH$_3$ or —O-SO$_2$CH$_3$) by methods well known in the art.

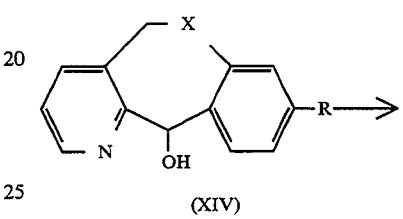

(XIV)

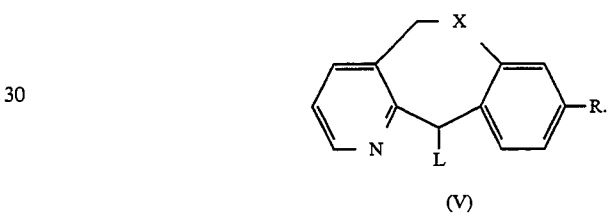

(V)

The alcohol XIV in turn may be obtained from the corresponding ketone VII via a variety of reductive methods. Various reducing agents, such as lithium aluminum hydride, sodium borohydride, lithium and the like, may be used for this conversion. The choice of solvent and temperature of the reaction mixture usually depends on the reducing agent employed and the selection of the appropriate conditions is well within the capabilities of those skilled in the art.

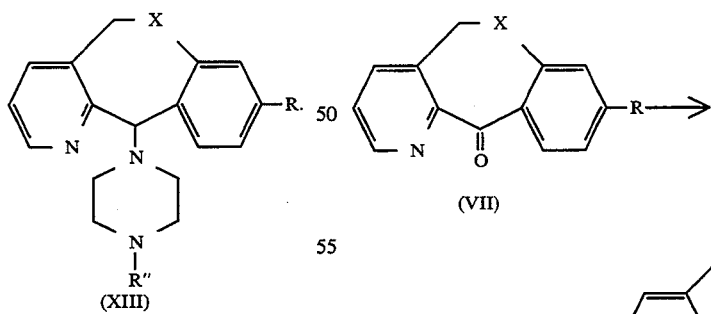

(VII)

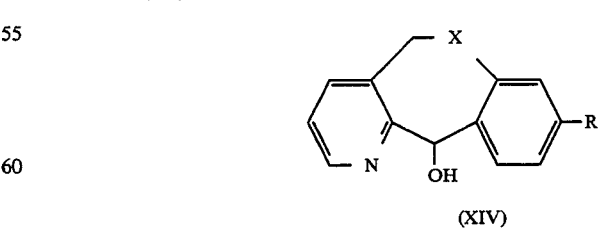

(XIV)

Preparation of Ketone VII Wherein X is Oxygen or Sulfur

There are many methods known in the art that may be employed for the preparation of substituted ketones of Formula VII. For example, the ketones of Formula VII can be prepared via an intramolecular cyclization of the corresponding nitrile of Formula XV. This transformation may be accomplished using a strong acid, such as trifluoromethanesulfonic acid. A wide range temperatures may be employed, for example, about −15° to about 100° C. The addition of water or aqueous acid to the reaction mixture is necessary following the cyclization in order to effect hydrolysis of the resultant imine to the corresponding ketone of Formula VII. Alternatively, an intramolecular Friedel-Crafts acylation of the acid chloride of Formula XVI may also provide the desired ketone of formula VII. The reaction may be carried out under usual Friedel-Crafts conditions in an inert solvent and in the presence of a Lewis acid such as aluminum chloride. The necessary acid chloride of Formula XVI may be obtained from the nitrile of Formula XV by the nitrile's hydrolysis to the corresponding carboxylic acid with aqueous acid (e.g., aqueous hydrochloric acid with heating) followed by its conversion to the acid chloride of Formula XVI by standard conditions (e.g., thionyl chloride or oxalyl chloride) well known to those skilled in the art.

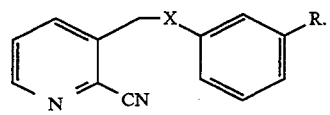

Alternatively, if L is a hydroxyl group in the compound of Formula XVII and X is an oxygen in the compound of Formula XVIII, then these compounds may be coupled using known in the art Mitsunobe conditions. For example, the compounds of Formulas XVII and XVIII may be coupled to produce a compound of Formula XV, where X is oxygen, using triphenylphosphine and diethyl azadicarboxylate in and inert dry solvent such as tetrahydrofuran. The reaction may usually be conducted at or below 0° C. (e.g., about −15° to about 0° C.); however, the reaction may also be heated to reflux.

The required alkyl halide of Formula XVII (X is halogen) can be obtained from the corresponding 3-methyl-2-cyanopyridine of Formula XIX. Halogenation of the compound of Formula XIX can best be accom-

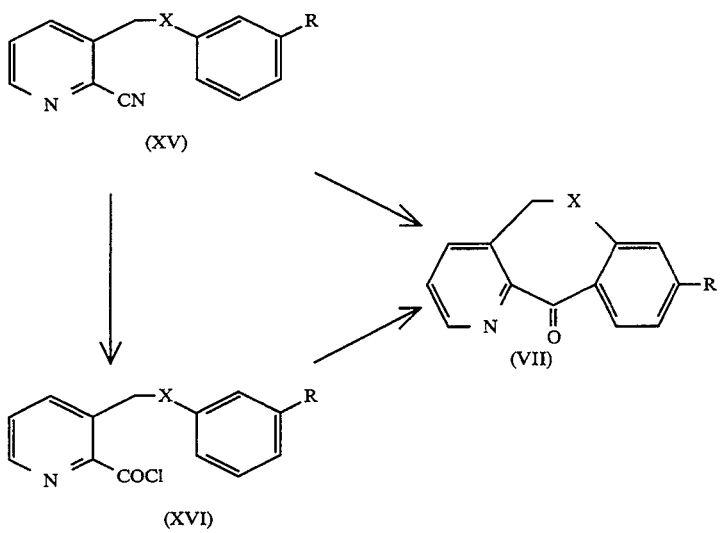

Compounds of Formula XV can generally be prepared by reaction of an alkyl halide of Formula XVII (wherein L is a suitable leaving group) with a compound of Formula XVIII. Those skilled in the art will appreciate that these displacements may be conducted at a variety of temperatures (usually between room temperature and 100° C.) in the presence of a base and a suitable polar solvent. Representative examples of bases include cesium carbonate (wherein acetone may be used as the polar solvent) or sodium hydride (wherein tetrahydrofuran may be used as the polar solvent).

plished under free radical conditions using, for example, N-bromosuccinamide to provide the bromide (X=Br), or sulfuryl chloride to provide the chloride (X=Cl). These reactions are carded out in an inert solvent, such as carbon tetrachloride, either in the presence of an initiator, such as aza(bis)isobutyronitrile (ABIN), and heat (T>50° C.) or light. Alternatively, a compound of Formula XVII, wherein X is a hydroxyl group, may be obtained from the corresponding carboxylic acid of Formula XX using reductive conditions which do not result in reduction of the cyano group (e.g., diborane in tetrahydrofuran) as is well known in the art.

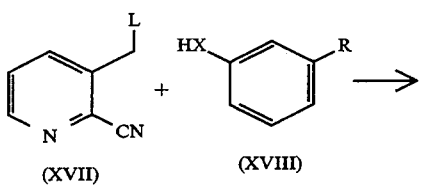

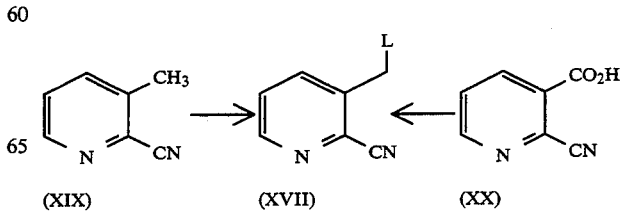

Preparation of Piperazine VI

Compounds of the Formula XXI can be prepared by coupling a compound of the Formula III with a compound of the Formula XII. This can be accomplished using a coupling agent such as DEC wherein L of compound III is a hydroxyl group or by direct acylation in the presence of base when L of compound III is a good leaving group, such as when L is halogen. The details of these coupling methods is described above in Processes A and B. Note that when R" is hydrogen then compound XXI is the same as compound VI. However, if R" is a carbamate then the carbamate must be subsequently removed in order to provide compound VI. This is accomplished in the same manner as described above for the conversion of compound VIII to compound IIA.

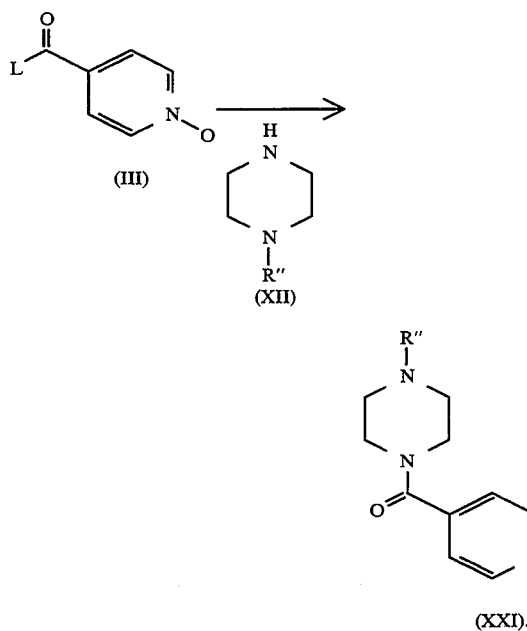

In the above processes, it is sometimes desirable and/or necessary to protect certain groups during the reactions. Certain protecting groups are employed in the above processes but, as those skilled in the art will recognize, other protecting groups may be used in their place. Conventional protecting groups are operable as described in Greene, T. W., "Protective Groups In Organic Synthesis," John Wiley & Sons, New York, 1981, the disclosure of which is incorporated herein by reference thereto. After the reaction or reactions, the protecting groups may be removed by standard procedures.

The compounds of the invention possess plateletactivating factor ("PAF") antagonistic properties. The compounds of the invention are, therefore, useful when PAF is a factor in the disease or disorder. This includes allergic diseases such as asthma, respiratory distress syndrome, urticaria and inflammatory diseases such as rheumatoid arthritis and osteo-arthritis. For example, PAF is an important mediator of such processes as platelet aggregation, smooth muscle contraction (especially in lung tissue), vascular permeability and neutrophil activation. Recent evidence implicates PAF as an underlying factor involved in airway hyperreactivity. The PAF antagonistic properties of these compounds may be demonstrated by use of standard pharmacological testing procedures as described below. These test procedures are standard tests used to determine PAF antagonistic activity and to evaluate the usefulness of said compounds for counteracting the biological effects of PAF. The in vitro assay is a simple screening test, while the in vivo test mimics clinical use of PAF antagonists to provide data which simulates clinical use of the compounds described herein.

A. IN VITRO STUDIES

Platelet Aggregation Assay

Platelet-activating factor (PAF) causes aggregation of platelets by a receptor-mediated mechanism. Therefore, PAF-induced platelet aggregation provides a simple and convenient assay to screen compounds for PAF antagonism. Human blood (50 mL) was collected from healthy male donors in an anticoagulant solution (5 mL) containing sodium citrate (3.8%) and dextrose (2%). Blood was centrifuged at 110$\times$g for 15 min. and the supernatant platelet-rich plasma (PRP) carefully transferred into a polypropylene tube. Platelet-poor-plasma (PPP) was prepared by centrifuging PRP at 12,000$\times$g for 2 min. (Beckman Microfuge B). PRP was used within 3 hr. of drawing the blood. PAF was dissolved in chloroform:methanol (1:1, v/v) at a concentration of 2 mg/mL and stored at $-70°$ C. An aliquot of this solution was transferred to a polypropylene tube and dried under a flow of nitrogen gas. To the dried sample was added Hepes-saline-BSA (BSA=bovine serum albumen) buffer (25 mM Hepes, pH 7.4, 1254 mM NaCl, 0.7 mM $MgCl_2$ and 0.1% BSA) to obtain a 1 mM solution and sonicated for 5 min. in a bath sonicator. This stock solution was further diluted to appropriate concentrations in Hepes-saline-BSA buffer. Collagen (Sigma) and adenosine diphosphate (ADP) (Sigma) were purchased as solutions. Test compounds were initially dissolved in dimethyl sulfoxide (DMSO) at a concentration of 50 mM and then further diluted in Hepes-saline-BSA buffer to achieve appropriate concentrations.

When an aggregating agent such as PAF is added to PRP, platelets aggregate. An aggregometer quantifies this aggregation by measuring and comparing light (infra-red) transmission through PPP and PRP. Aggregation assays were performed using a dual-channel aggregometer (Model 440, Chrono-Log Corp., Havertown, Pa.). PRP (0.45 mL) in aggregometer cuvettes was continually stirred (37° C.). Solutions (50 $\mu$L) of test compounds or vehicle were added to the PRP and, after incubation for 2 min., 10–15 $\mu$l aliquots of PAF solution were added to achieve a final concentration of $1-5 \times 10^{-8}$M. In different experiments the aggregatory response was kept within a set limit by varying the concentration of PAF. Incubations were continued until the increase in light transmission reached a maximum (usually 2 min.). This increase in light transmission reflecting platlet aggregation is transmitted to a computer by the Chrono-Log model 810 AGGRO/LINK interface. The AGGRO/LINK calculates the slope of transmission change, thus providing the rate of aggregation. Values for inhibition were calculated by comparing rates of aggregation obtained in the absence and the presence of the compound. For each experiment, a standard PAF antagonist such as 8-chloro-6,11-dihydro-11-(1-acetyl-4-piperidylidene)-5H-benzo[5,6]cyclohepta[1,2-b]pyridine was used as a positive control.

Compounds that inhibit PAF-induced aggregation were tested against several other aggregating agents including collagen (0.2 mg/mL) and ADP (2 μM). Compounds showing no activity against these latter agents were considered to be specific PAF antagonists. Results are shown in TABLE 1 below.

B. In Vivo Studies: Agonist-Induced Responses

Spasmogen-Induced Bronchospasm in Guinea Pigs

Male Hartley guinea pigs (450–550 g) were obtained from Charles River Breeding Laboratories. The animals were fasted overnight and the following day were anesthetized with 0.9 mL/kg i.p. of dialurethane (containing 0.1 g/mL diallylbarbituric acid, 0.4 g/mL ethylurea and 0.4 g/mL urethane). The left jugular vein was cannulated for the administration of compounds. The trachea was cannulated and the animals were ventilated by a rodent respirator at 55 strokes/min. with a stroke volume of 4 mL. A side arm to the tracheal cannula was connected to a pressure transducer to obtain a continuous measure of inflation pressure. Bronchoconstriction was measured as the percent increase in inflation pressure that peaked within 5 min. after challenge with spasmogen. The animals were challenged i.v. with either histamine (10 ug/kg) or PAF (0.4 μg/kg in isotonic saline containing 0.25% BSA). Each animal was challenged with only a single spasmogen. The effect of a compound on the bronchospasm is expressed as a percent inhibition of the increase in inflation pressure compared to the increase in a control group. Results are shown in Table 1 below.

In Table 1 the column "No." represents "Compound Numbers" and Compound Numbers 1 to 5 in Table 1 refer to:

(a) Compound No. 1 is disclosed in WO 88/03138, discussed above, and has the structure:

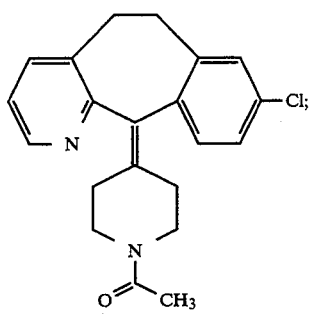

(b) Compound No. 2 is disclosed in WO 90/13548, discussed above, and has the structure:

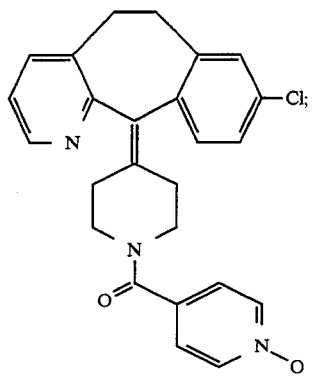

c) Compound No. 3, a compound of the invention, has the structure:

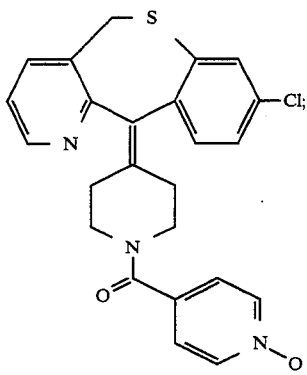

(d) Compound No. 4, a compound of the invention, has the structure:

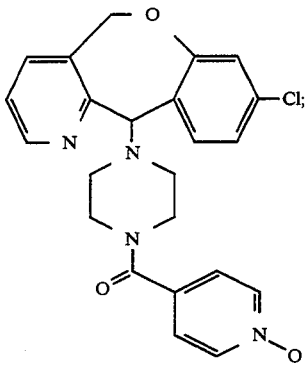

and (e) Compound No. 5, a compound of the invention, has the structure:

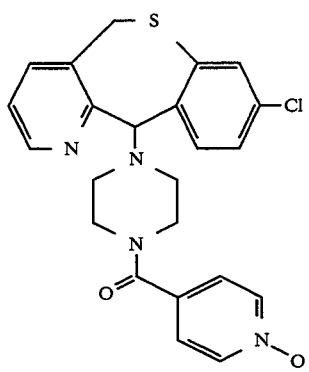

TABLE 1

| No. | PAF Antagonism (in vitro) IC$_{50}$ (μM) | Agonist Bronchospasm (in vivo)-Oral[a] | | | |
|---|---|---|---|---|---|
| | | PAF | | Histamine | |
| | | Dose (mg/kg) | Inhibition (%) | Dose (mg/kg) | Inhibition (%) |
| 1 | 0.6 | 5 | 49 | 3 | 49 |
| 2 | 0.2 | 3 | 93 | 3 | 37 |
| 3 | 0.04 | 1 | 91 | 10 | 9 |
| 4 | 0.2 | 1 | 68 | 3 | 5 |
| 5 | 0.3 | 1 | 38 | 10 | 9 |

[a] % inhibition 2 hours after dose of drug

The data in Table 1 demonstrate that the compounds of this invention (e.g., Compound Numbers 3–5 in Table 1) are much more selective in their antagonism of PAF (i.e., they are weak antihistamines) than previous compounds of this structural type. For example, Compounds 3–5 are active against the PAF response at a dose of 1 mg/kg orally, but even at higher doses (3–10 mg/kg) Compounds 3–5 have no effect on the response to histamine. This contrasts with Compounds 1 and 2 where there is an effect on both responses at similar doses.

For preparing pharmaceutical compositions from the compounds described by this invention, inert, pharmaceutically acceptable carders can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example there may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carder, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 500 mg, according to the particular application. The appropriate dosage can be determined by comparing the activity of the compound with the activity of a known antihistaminic compound such as 8-chloro-6,11-dihydro-11-(1-ethoxycarbonyl-4-pipeddylidene)-5H-benzo[5,6]cyclohepta[1,2-b]pyridine, which compound is disclosed in U.S. Pat. No. 4,282,233.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 1500 mg/day, preferably 10 to 750 mg/day, in two to four divided doses to achieve relief of the symptoms. The compounds are non-toxic when administered within this dosage range.

The following examples are intended to illustrate, but not to limit, the present invention.

PREPARATIVE EXAMPLE 1

A. 2-CYANO-3-(BROMOMETHYL)PYRIDINE

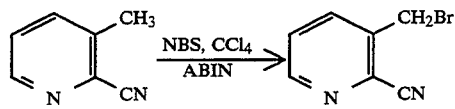

Combine 2-cyano-3-methylpyridine (11.8 g), N-bromosuccinimide (NBS) (26.8 g, 1.5 eq.) and aza(bis-)isobutyronitrile (ABIN) (180 mg) in dry CCl$_4$ (300 mL). Reflux the mixture overnight. Pour the mixture into water, basify with NaOH and extract with CH$_2$Cl$_2$. Wash the organic portion with water, dry (Na$_2$SO$_4$), filter and concentrate to obtain a liquid. Chromatograph the product, eluting with 30% diethyl ether in hexanes. Combine the appropriate fractions to obtain the mono-bromo compound (5.01 g) as a yellowish solid: m.p. 41.5°–42.5° C.

B.

2-CYANO-3-(3-CHLOROPHENOXYMETHYL)-PYRIDINE

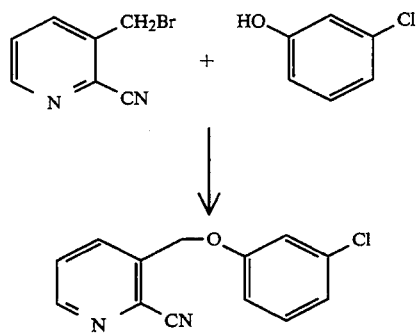

Stir a solution of the title compound of part A above (0.71 g, 3.6 mmol), NaI (54 mg, 0.1 eq) and Cs$_2$CO$_3$ (1.17 g, 1.0 eq) in dry acetone (17 mL, predried over MgSO$_4$) at room temperature for 5 minutes, then add 3-chlorophenol (463 mg) via a syringe. Reflux in an oil bath for 4.5 hours. Filter and wash the filtrate with dry acetone. Concentrate the filtrate, suspend in diethyl ether, and refilter to obtain a brown solid which is the title compound in crude form. Triturate with pentane, and resuspend in diisopropyl ether (40 mL) with charcoal, and heat on a steam bath. Filter and evaporate the solvent to obtain the title compound, which crystallizes to form a white solid (640 mg): m.p. 70°–72° C.

C. 8-CHLORO-5,11-DIHYDRO[1]BENZOX-EPINO[4,3-B]PYRIDIN-11-ONE

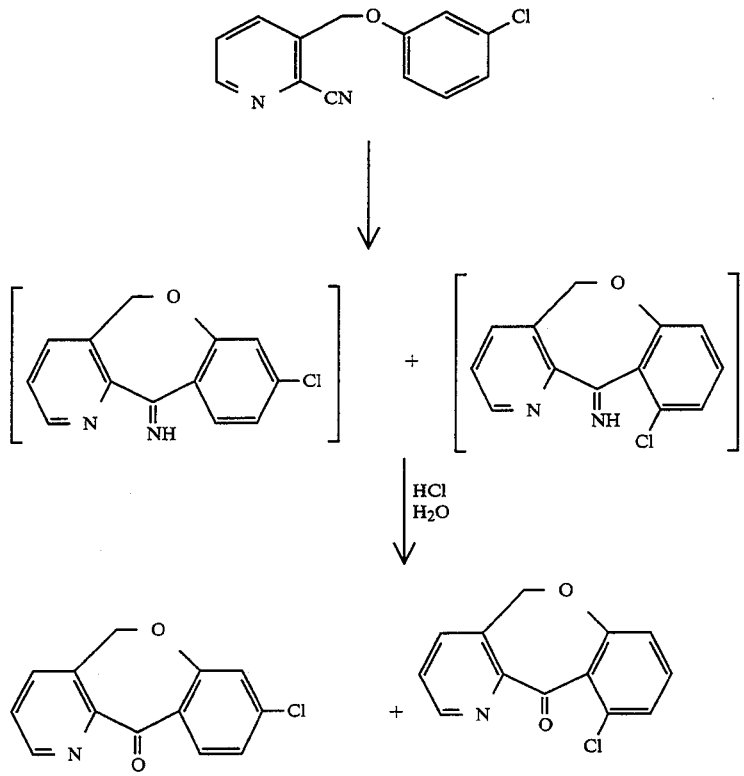

Stir the title compound from part B above (6.1 g) in CF$_3$SO$_3$H (60 mL) at room temperature for 3 hours. Upon completion, quench with H$_2$O and conc. HCl (30%) and continue stirring for 0.5 hours. Warm to 35° C. for 0.5 hours. Basify with NaOH (25%) and extract with CH$_2$Cl$_2$ (2×). Wash with brine (2×), filter and dry over Na$_2$SO$_4$, and concentrate in vacuo to afford a semi-solid. Triturate the resulting semisolid (6.35 g) with diisopropyl ether and separate the isomers via flash chromatography (30% ethyl acetate in hexanes). Combine the appropriate fractions to obtain the title compound as a solid (4.902 g): m.p. 139.5°–140.5° C., and the 10-chloro compound as a solid (498 mg): m.p. 100°–102° C.

D. 8-CHLORO-5,11-DIHYDRO[1]BENZOX-EPINO[4,3-b]PYRIDIN-11-OL

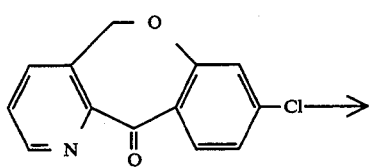

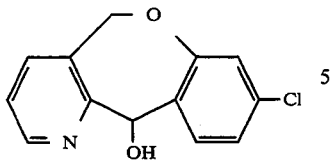

Add sodium borohydride (0.96 g, 25.4 mmole) to 8-chloro[1]benzoxepino[4,3-b]pyridin-11-one (10.00 g, 40.7 mmole) in ethanol (100 mL). Stir for 18 hours at room temperature. Add water (100 mL), and concentrate in vacuo. Add additional water (100 mL), and extract with dichloromethane. Wash the organic solution with saturated NaCl, dry with MgSO4, filter, and concentrate in vacuo. Dissolve the oil in dichloromethane, and chromatograph on silica gel, eluting with 50% ethyl acetate in hexane. Combine the appropriate fractions, and concentrate under reduced pressure to give a white solid (8.50 g, 84% yield): mp 105°-108° C.

E.
8,11-DICHLORO-5,11-DIHYDRO[1]BENZOXEPINO[4,3-b]PYRIDINE

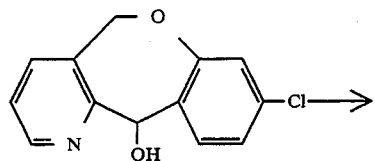

Add thionyl chloride (2.74 mL, 4.48 g, 37.6 mmole) to 8-chloro-5,11-dihydro[1]benzoxepino[4,3-b]pyridin-11-ol (8.48 g, 34.2 mmole) in dichloromethane (100 mL) at 0° C. under a nitrogen atmosphere. Stir for 30 minutes at 0° C., and then stir for 60 minutes at room temperature. Add iced 1.5N NaOH (100 mL), and separate layers. Extract aqueous solution with dichloromethane (2×100 mL). Wash the combined organic solution with water and saturated NaCl, dry with MgSO4, filter, and concentrate in vacuo to give a reddish-black oil (8.82 g, 97% yield).

F.
8-CHLORO-5,11-DIHYDRO-11-(1-PIPERAZINYL)[1]BENZOXEPINO[4,3-b]PYRIDINE

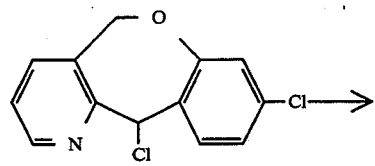

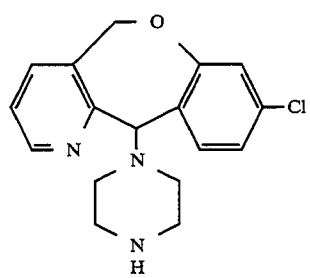

Add 8,11-dichloro-5,11-dihydro[1]benzoxepino[4,3b-]pyridine (8.81 g, 0.033 mole) in dry tetrahydrofuran (150 mL) dropwise via addition funnel to piperazine (33.37 g, 0.387 mole) in dry tetrahydrofuran (300 mL) under a nitrogen atmosphere. Stir for 4 hours at room temperature, and concentrate in vacuo. Add ice cold 1.5N aqueous NaOH (200 mL), and extract with ethyl acetate (3×125 mL). Wash the organic solution with water and saturated NaCl, dry with MgSO4, filter, and concentrate in vacuo. Dissolve the oil in dichloromethane, and chromatograph on silica gel, eluting with 90:9:1 dichloromethane:methanol:NH4OH. Combine the appropriate fractions, and concentrate under reduced pressure to give a tan solid (6.41 g, 61% yield): mp 162°-164° C.

PREPARATIVE EXAMPLE 2

A.
2-CYANO-3-(3-CHLOROPHENYLTHIOMETHYL)PYRIDINE

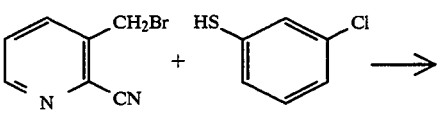

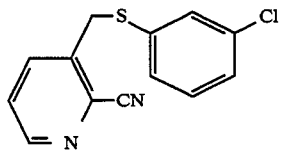

To a stirred, cloudy solution of sodium methoxide (14.7 g, 0.27 mol) in methanol (450 mL), contained in a water bath, add a solution of 3-chlorothiophenol (39.5 g, 0.27 mol) in methanol (95 mL). To the resultant solution add a solution of 2-cyano-3-(bromomethyl)pyridine (48.9 g, 0.25 mol) in methanol (195 mL), and stir the reaction mixture at room temperature for 1 h. Concentrate the reaction mixture under reduced pressure, add 500 mL of ether to the residue, stir, and filter to remove the sodium bromide. Evaporate ether under reduced pressure to obtain the title compound as an amber oil, which may be used without further purification.

B.
8-CHLORO-5,11-DIHYDRO[1]BENZO-THIEPINO[4,3-b]PYRIDIN-11-ONE

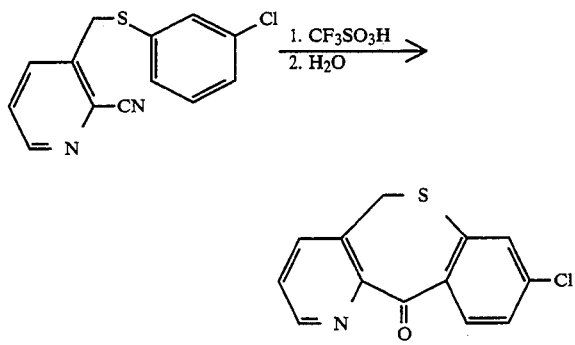

Stir a solution of the title compound from Part A above (49.7 g, 0.19 mol) in trifluoromethanesulfonic acid (500 mL) for 3.5 h at 95° C. Allow the reaction mixture to cool below 60° C. and pour onto crushed ice (1500 mL). Stir the mixture for 0.5 h and add sufficient aqueous sodium hydroxide (220 mL of 50% solution) to raise the pH to 9. Extract the aqueous solution with ethyl acetate (1×), saturate with sodium chloride, and extract again (2×) with ethyl acetate. Wash the combined organic extracts with brine (3×), filter, and dry over anhydrous MgSO$_4$. Filter and remove the solvent under reduced pressure. Chromatograph the residual material on silica gel, eluting with ethyl acetate/hexanes (3:2), to obtain the title ketone as a tan solid: m.p. 186°–187° C.

C.
1-METHYL-4-(8-CHLORO-11-HYDROXY-5,11-DIHYDRO[1]BENZOTHIEPINO-[4,3-b]PYRIDINYL)PIPERIDINE

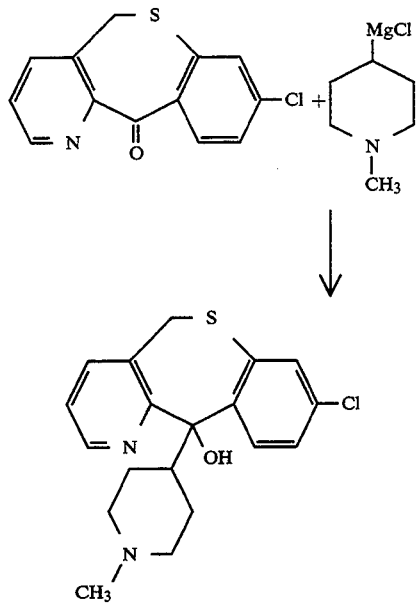

With cooling in an ice-water bath, add a suspension of the title ketone from Part B above (13.4 g, 51.2 mmol) in dry tetrahydrofuran (52 mL) to a stirred solution (55 mL of approximately 1M) in THF of the Grignard reagent derived from 1-methyl-4-chloropiperidine. Stir the resultant mixture for 1 h at room temperature. Quench the reaction by cooling the mixture to 10° C. in an ice-water bath and adding saturated aqueous ammonium chloride solution (50 mL). Add methylene chloride (100 mL), and stir the mixture for a few minutes. Filter the mixture through Celite, and wash the filter cake with methylene chloride. Combine the original filtrate and washes, separate the organic phase, and extract the aqueous phase (2×) with additional methylene chloride. Combine the organic extracts, wash with brine (2×75 mL), and dry over anhydrous sodium sulfate. Filter, strip the filtrate under reduced pressure, and chromatograph the residue on silica gel, eluting with methylene chloride/methanol/ammonium hydroxide (90:9:0.5), to obtain the title compound as an off-white to pale pink solid: m.p. 158.5°–159.5° C.

D.
1-METHYL-4-(8-CHLORO-5,11-DIHYDRO[11-]BENZOTHIEPINO[4,3-b]PYRIDIN-11-YLIDENE)PIPERIDINE

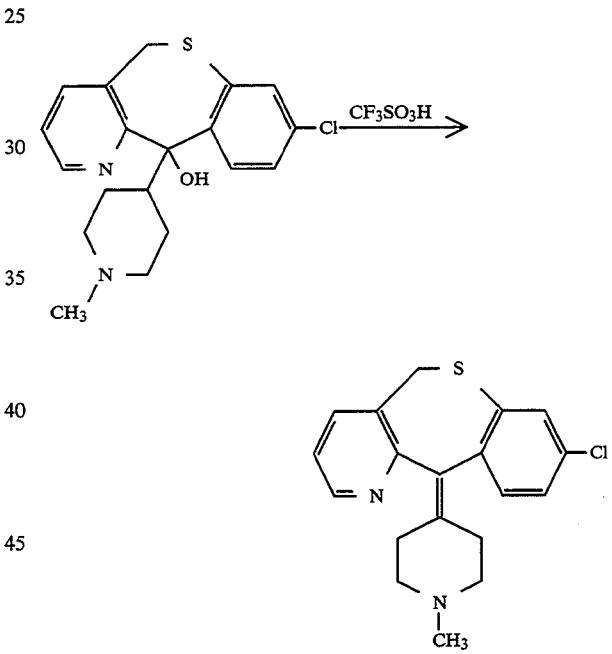

Heat a solution of the title compound from Part C above (5.04 g, 13.9 mmol) in trifluoromethanesulfonic acid at 45° C. for 10.5 h. Cool the reaction solution to room temperature, and pour it into a stirred ice-water mixture. Maintain cooling in an ice-water bath, and add with stirring aqueous sodium hydroxide (130 mL of a 50% solution). Extract the solution with methylene chloride (3×), wash the combined extracts successively with water (2×) and brine (1×), dry over anhydrous sodium sulfate, and evaporate solvent under reduced pressure. Purify the residual glass by chromatographing on silica gel, eluting with methyene chloride/methanol-/ammonium hydroxide (90:9:0.25), and triturating the solid in acetonitrile. Filter to obtain the title compound as a light tan solid, containing 0.08 mole methylene chloride: m.p. 175°–177° C.

E. 1-ETHOXYCARBONYL-4-(8-CHLORO-5,11-DIHYDRO[1]BENZOTHIEPINO[4,3-b]PYRIDIN-11-YLIDENE)PIPERIDINE

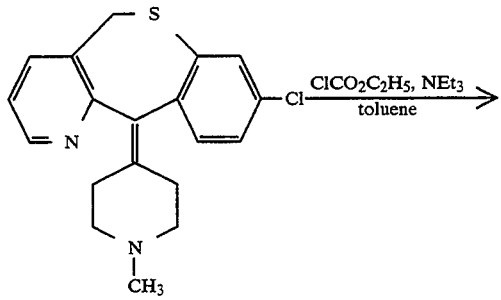

To a stirred solution of the title compound from Part D above (1.44 g, 4.2 mmol) and triethylamine (966 mg, 9.5 mmol) in dry toluene (27 mL), maintained at 80° C., add dropwise ethyl chloroformate (2.78 g, 25.6 mmol). After one hour, add more triethylamine (480 mg, 4.7 mmol), and continue heating at 80° C. for an additional hour. Cool the reaction mixture to 50° C., add ethyl acetate (15 mL), wash successively with water (2×) and brine (1×), and dry over anhydrous magnesium sulfate. Filter, evaporate the filtrate under reduced pressure, and purify by chromatographing the residual solid on silica gel. Elute first with ethyl acetate/hexanes (9:1); then rechromatograph the partially purified material with ethyl acetate/hexanes (1:1) to obtain the title compound as an off-white solid: m.p. 154°–157° C.

F. 4-(8-CHLORO-5,11-DIHYDRO[1]BENZOTHIEPINO[4,3-b]PYRIDIN-11-YLIDENE)PIPERIDINE

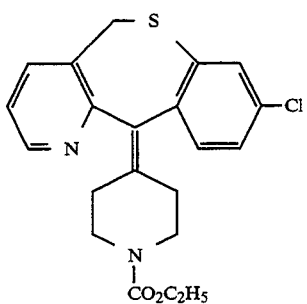

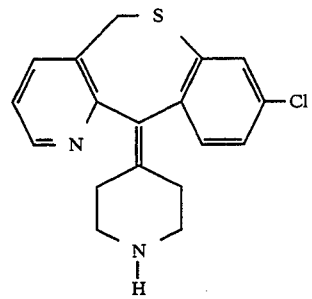

Reflux for 21.5 h in an inert gas atmosphere a solution of the title compound from Part E above (720 mg, 1.87 mmol) and potassium hydroxide (2.0 g, 35.6 mmol) in ethanol (20 mL) and water (2 mL). Cool to room temperature, dilute with methylene chloride (20 mL), and wash successively with water (4×) and brine (1×). Dry the solution over anhydrous sodium sulfate, filter, and evaporate the filtrate under reduced pressure to obtain the title compound as an off-white solid: m.p. 206.5°–215° C.

PREPARATIVE EXAMPLE 3

A. 8-CHLORO-5,11-DIHYDRO[1]BENZOTHIEPINO[4,3-b]PYRIDIN11-OL

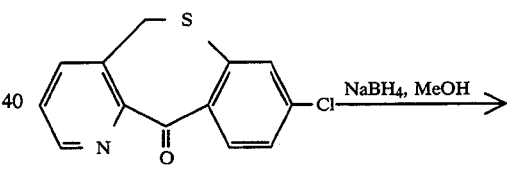

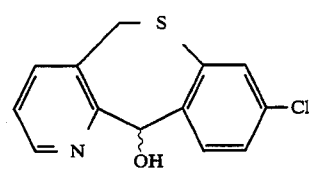

Add sodium borohydride (2.60 g, 0.0688 mol) portionwise over 15 minutes to a stirred suspension of 8-chloro-5,11-dihydro[1]benzothiepino[4,3-b]pyridin-11-one (15.0 g, 0.0573 mol) in methanol (150 mL) at 25°–35° C. and under an atmosphere of nitrogen. Stir the mixture for 40 minutes at 25°–30° C. Concentrate the mixture in vacuo to provide a suspension, and then pour it into water (150 mL), and extract with CH$_2$Cl$_2$ (3×100 mL). Combine the extracts, wash with water (3×75 mL), dry over Na$_2$SO$_4$, filter, and concentrate in vacuo. Purify the crude product (18.4 g) via flash chromatography by eluting with EtOAc/hexanes (1:1) to obtain the title compound (9.70 g, 64% yield).

B. 8,11-DICHLORO-5,11-DIHYDRO[1]BENZO-THIEPINO[4,3-b]PYRIDINE

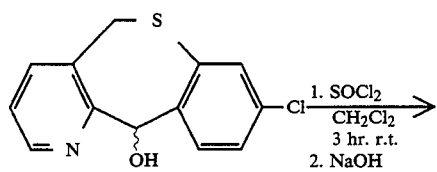

Add thionyl chloride (3.1 mL, 0.0425 mol) dropwise to a stirred suspension of 8-chloro-5,11-dihydro[1]benzothiepino[4,3-b]pyridin-11-ol (8.8 g, 0.0334 mol) in CH$_2$Cl$_2$ (75 mL) at 3°–8° C. Stir the mixture at room temperature for 3 hours, and pour it into 150 mL of 2.5M NaOH containing ice. Filter, separate the aqueous layer and extract it with CH$_2$Cl$_2$ (2×50 mL). Combine the organic extracts, and wash with water (3×50 mL) and brine (1×75 mL). Dry the mixture over MgSO$_4$, filter, and concentrate in vacuo to obtain the title compound (8.0 g, 80%).

C. 8-CHLORO-5,11-DIHYDRO-11-(1-PIPERAZINYL)[1]BENZOTHIEPINO[4,3-b]PYRIDINE

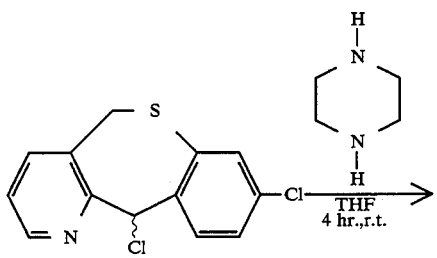

Add a solution of 8,11-dichloro-5,11-dihydro[1]benzothiepino[4,3-b]pyridine (8.15 g, 0.029 mol) in tetrahydrofuran (100 mL) to a stirred suspension of piperazine (28.9 g, 0.34 mol) in tetrahydrofuran (290 mL) at 18°–19° C. over 20 minutes. Stir the mixture for 4 hours at room temperature and then pour it into 2.5M aqueous NaOH (250 mL) containing ice. Separate the layers, and extract the aqueous portion with EtOAc (3×100 mL). Combine the organic portions, and wash with H$_2$O (3×75 mL) and brine (150 mL). Dry the mixture over MgSO$_4$, filter, and concentrate the organic layer in vacuo to obtain the crude product (8.9 g). Purify the crude product via flash chromatography (9:1:0.125 CH$_2$Cl$_2$/MeOH/NH$_4$OH) to obtain the title compound (7.6 g, 78% yield).

EXAMPLE 1

4-(8-CHLORO-5,11-DIHYDRO[1]BENZO-THIEPINO[4,3-b]PYRIDIN-11-YLIDENE)-1-(4-PYRIDINYLCARBONYL)PIPERIDINE N$^1$-OXIDE

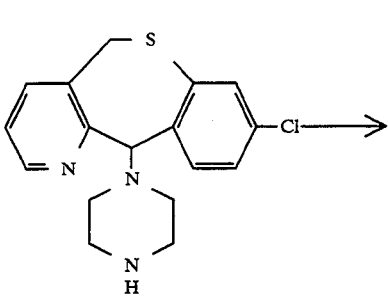

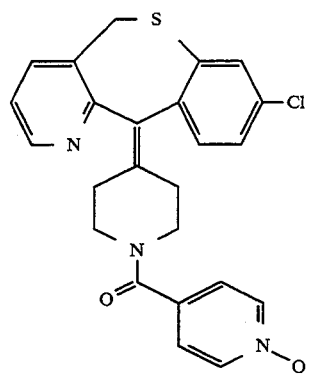

To a stirred suspension of 8-chloro-5,11-dihydro-11-(1-piperazinyl)[1]benzothiepino[4,3-b]pyridine (1.9 g, 5.73 mmol) and isonicotinic acid N-oxide (0.95 g, 6.83 mmol) in dry dichloromethane (60 mL), add 1-hydroxybenzotriazole hydrate (0.93 g, 6.88 mmol) and 1-(3-dimethylaminopropyl)-3-ethylcarbodiimide hydrochloride (1.32 g, 6.89 mmol). Stir the resultant mixture at room temperature for 20 hours; then introduce additional quantities of the benzotriazole (0.19 g, 1.43 mmol) and carbodiimide (0.27 g, 1.43 mmol), and continue stirring for another 6 hours at room temperature. Wash the reaction mixture successively with 2.5M aqueous sodium hydroxide (15 mL), water (3×10 mL), and brine (15 mL). Dry the washed solution over anhydrous magnesium sulfate, filter out the drying agent, and remove solvent from the filtrate under reduced pressure. Flash chromatograph the residue on silica gel, eluting with dichloromethane/methanol/ammonium hydroxide (95:5:0.125) to obtain the title compound as a hemihydrate (2.29 g, 88% yield): m.p. 167°–169° C. (dec); MS (FAB) m/z 453 [M$^+$+1].

EXAMPLE 2

1-(8-CHLORO-5,11-DIHYDRO[1]BENZOX-EPINO[4,3-b]PYRIDIN-11-YL)-4-(4-PYRIDINYL-CARBONYL)PIPERAZINE N⁴-OXIDE

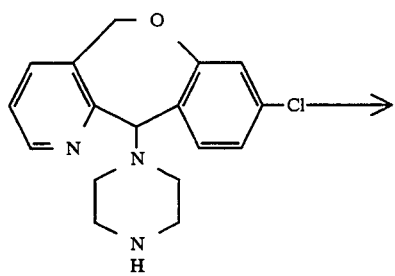

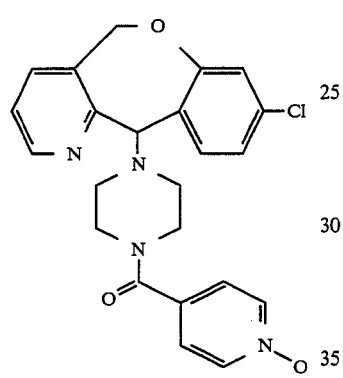

Add isonicotinic acid N-oxide (0.79 g, 5.70 mmole) to 8-chloro-5,11-dihydro-11-(1-piperazinyl)[1]benzoxepino[4,3-b]pyridine (1.50 g, 4.75 mmole) in dichloromethane (30 mL) at 0° C. under a nitrogen atmosphere. Add 1-hydroxybenzotriazole hydrate (0.77 g, 5.70 mmole) and 1-(3-dimethylaminopropyl)-3-ethylcarbodiimide hydrochloride (1.09 g, 5.70 mmole). Warm the reaction mixture up slowly, and stir for 23 hours at room temperature. Add 1N aqueous sodium hydroxide (50 mL), and separate layers. Extract with dichloromethane (2×50 mL). Wash the organic solution with brine, dry with MgSO₄, filter, and concentrate under reduced presure. Dissolve the solid in dichloromethane, and chromatograph on silica gel, eluting with 7% methanol in dichloromethane, then 10% methanol in dichloromethane. Combine the appropriate fractions, and concentrate under reduced pressure to give a light yellow solid. Recrystallize the product from dichloromethane/hexane to obtain the title compound as a white solid (1.97 g, 95% yield): mp 206°-208° C.; MS (CI) m/z 421 [M⁺−16].

EXAMPLE 3

1-(8-CHLORO-5,11-DIHYDRO[1]BENZO-THIEPINO[4,3-b]PYRIDIN-11-YL)-4-(4-PYRIDINYLCARBONYL)PIPERAZINE N⁴-OXIDE

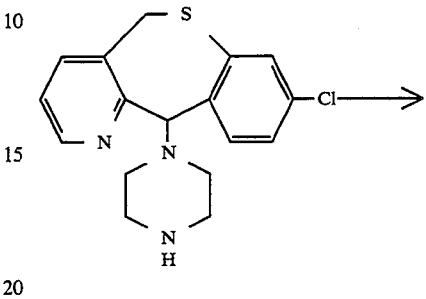

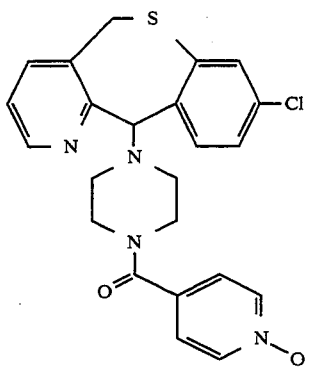

To a stirred suspension of 8-chloro-5,11-dihydro-11-(1-piperazinyl)[1]benzothiepino[4,3-b]pyridine (251 mg, 0.762 mmol) and isonicotinic acid N-oxide (128 mg, 0.918 mmol) in dry dichloromethane (20 mL), add 1-hydroxybenzotriazole hydrate (123 mg, 0.909 mmol) and 1-(3-dimethylaminopropyl)-3-ethylcarbodiimide hydrochloride (175 mg, 0.912 mmol). Stir the resultant mixture at room temperature for 3 hours. Wash the reaction mixture successively with 2.5M aqueous sodium hydroxide (5 mL), water (4×10 mL), and brine (15 mL). Dry the washed solution over anhydrous magnesium sulfate, filter out the drying agent, and remove solvent from the filtrate under reduced pressure. Flash chromatograph the residue on silica gel, eluting with methanol/dichloromethane (1:9) to obtain the title compound as a ¾ hydrate (240 mg, 70% yield): mp 162°-165.5° C. (melts to a viscous gum); MS (FAB) m/z 450 [M⁺+1].

The following are examples of pharmaceutical dosage forms which may contain a compound of the invention. As used herein, the term "active compound" is used to designate the compound 4-(8-chloro-5,11-dihydro[1]benzothiepino[4,3-b]pyridin-11-ylidene )-1-(4-pyridinylcarbonyl)piperidine N¹-oxide. The scope of the invention in its pharmaceutical composition aspect is not to be limited by the examples provided, since any other compound of structural Formula I can be substituted into the pharmaceutical composition examples.

Pharmaceutical Dosage Form Examples

Example A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|   | TOTAL | 300 | 700 |

Method of Manufacture

Mix Item Nos. 1 and 2 in a suitable mixer for 10-15 minutes. Granulate the mixture with Item No. 3. Mill the damp granules through a coarse screen (e.g., ¼") if needed. Dry the damp granules. Screen the dried granules if needed and mix with Item No. 4 and mix for 10-15 minutes. Add Item No. 5 and mix for 1-3 minutes. Compress the mixture to appropriate size and weight on a suitable tablet machine.

Example B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
|   | TOTAL | 250 | 700 |

Method of Manufacture

Mix Item Nos. 1, 2, and 3 in a suitable blender for 10-15 minutes. Add Item No. 4 and mix for 1-3 minutes. Fill the mixture into suitable two-piece hard gelatin capsules on a suitable encapsulating machine.

While the present invention has been described in connection with certain specific embodiments thereof, it will be evident to one of ordinary skill in the art that many alternatives, modifications and variations may be made. All such alternatives, modifications and variations are intended to be included within the spirit and scope of the invention.

What is claimed is:

1. A compound of Formula I:

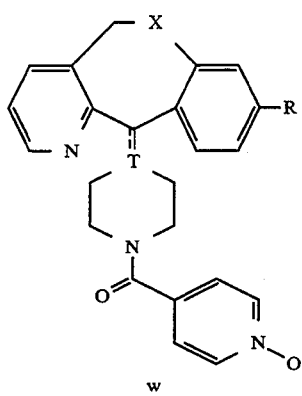

or a pharmaceutically acceptable salt or solvate thereof, wherein:

R is selected from the group consisting of: H, Cl, Br, F, and I;

T represents C or N with the dotted line attached to T representing a double bond when T is C and being absent when T is N; and X represents O or S with the proviso that T is N when X is O.

2. The compound of claim 1 wherein R is Cl.

3. A compound of Formula IA:

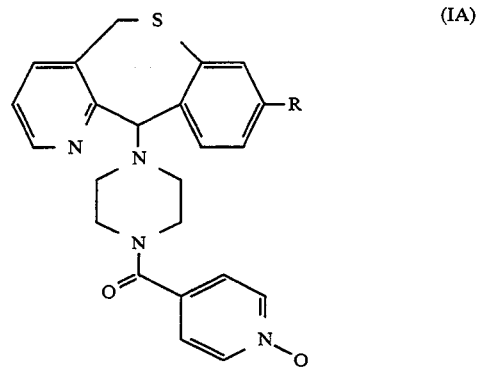

wherein R is selected from the group consisting of: H, Cl, Br, F, and I.

4. The compound of claim 3 wherein R is Cl.

5. A compound of the formula IB:

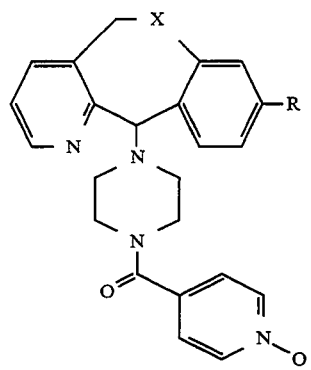

wherein X is selected from the group consisting of: O and S; and R is selected from the group consisting of: H, Cl, Br, F, and I.

6. The compound of claim 5 wherein X is O and R is Cl.

7. The compound of claim 5 wherein X is S and R is Cl.

8. A pharmaceutical composition comprising a compound of claim 1 in combination with a pharmaceutically acceptable carrier.

9. A method of treating asthma comprising administering to a mammal in need of such treatment an anti-asthmatic effective amount of a compound of claim 1.

10. A method of treating allergy comprising administering to a mammal in need of such treatment an anti-allergic effective amount of a compound of claim 1.

11. A method of treating inflammation comprising administering to a mammal in need of such treatment an anti-inflammatory effective amount of a compound of claim 1.

* * * * *